United States Patent [19]

Kane et al.

[11] 4,255,438

[45] Mar. 10, 1981

[54] METHOD FOR REDUCTION OF CARDIAC MORTALITY RATE USING PYRAZOLIDINE-3,5-DIONES

[75] Inventors: Sydney H. Kane, Warren; Erwin Margulies, Morganville, both of N.J.

[73] Assignee: Ciba-Geigy Corporation, Ardsley, N.Y.

[21] Appl. No.: 36,923

[22] Filed: May 7, 1979

Related U.S. Application Data

[63] Continuation-in-part of Ser. No. 897,973, Apr. 20, 1978, abandoned.

[51] Int. Cl.³ .......................................... A61K 31/415
[52] U.S. Cl. .................................. 424/273 P
[58] Field of Search .................................. 424/273 P

[56] References Cited

U.S. PATENT DOCUMENTS

| | | | |
|---|---|---|---|
| 2,700,671 | 1/1955 | Hafliger | 560/61 |
| 3,752,894 | 8/1973 | Esteve | 424/273 P |
| 3,760,080 | 9/1973 | Urwyler | 424/273 P |
| 3,833,729 | 9/1974 | Negrevergne | 424/273 P |

OTHER PUBLICATIONS

Platelets, Drugs & Thombosis Sym.—Blakely et al., pp. 284–291 (1972).
New Eng. J. Med. 298, pp. 289–295 (1978).

*Primary Examiner*—Douglas W. Robinson
*Attorney, Agent, or Firm*—Theodore O. Groeger

[57] ABSTRACT

Pharmaceutical compositions comprising a substituted pyrazolidine-3,5-dione, e.g. the 1,2-diphenyl-4-(2-phenylthioethyl or 2-phenylsulfinylethyl)-pyrazolidine-3,5-dione, or a salt thereof with a base, are useful in the treatment of cardiovascular diseases.

16 Claims, No Drawings

METHOD FOR REDUCTION OF CARDIAC MORTALITY RATE USING PYRAZOLIDINE-3,5-DIONES

CROSS-REFERENCE TO RELATED APPLICATION

This is a continuation-in-part of application Ser. No. 897,973, filed Apr. 20, 1978 now abandoned.

BACKGROUND OF THE DISCLOSURE

Orally applicable pharmaceutical compositions comprising about 50 to 200 mg of sulfinpyrazone, i.e. the 1,2-diphenyl-4-(2-phenylsulfinylethyl)-pyrazolidone-3,5-dione, as the active ingredient, are used as uricosuric agents (for nearly 20 years) and sold under GEIGY's brand name ANTURANE ®.

Moreover, according to Platelets, Drugs and Thrombosis Symp. Hamilton (Canada) 1972, pages 284–291 (Karger, Basel 1975) it is known that the oral administration of about 600 mg of sulfinpyrazone "per day in three divided doses . . . to . . . patients with the diagnosis of myocardial infarction, either along or in combination with a stroke" resulted only in about 10% difference in survival after one year and about 25% between 2.5 and 4 years. "There was no significant difference between the survival curves for the two treatment groups," however.

Compositions of said 1,2-diphenyl-4-(2-phenylthioethyl)-pyrazolidine-3,5-dione, or pharmaceutically acceptable salts thereof are also known according to Schweiz. Med. Wochenschrift 84, 1315 (1954) to exhibit antiphlogistic and analgetic effects, and hence can be used in the treatment of rheumatic arthritis. Oral doses of 1–2 g thereof per day, administered in 0.2 g single dosage units, caused an improvement of the arthritis in about ⅔ of clinical patients.

It is further known from J. Pharmacol. 119, 418 (1957) that said 1,2-diphenyl-4-(2-phenylthioethyl)-pyrazolidone-3,5-dione is metabolized in the human organism to sulfinpyrazone, which is considered as the effective component for all pharmacological effects of the former, which have hitherto been ascertained.

Surprisingly, according to the New England Journal of Medicine, 298, pages 289–295 (February 9, 1978) "a randomized, double-blind, multicenter clinical trial comparing sulfinpyrazone (200 mg four times a day) and placebo in the prevention of cardiac mortaility among patients with a recent documented myocardial infarction" established the following results: "For cardiac deaths . . . an observed reduction of 48.5 percent" and "a 57.2 percent reduction in sudden-cardiac-death rate," with the highly significant $P=0.018$ or 0.015 values, respectively.

Moreover, it has been surprisingly established that 1,2-diphenyl-4-(2-phenylthioethyl)-pyrazolidine-3,5-dione, and said salts thereof, are excellently suitable for compositions in the treatment of cardiovascular diseases, particularly in conditions caused by an abnormal function of the blood platelets, such as in the treatment of thrombotic diseases.

SUMMARY OF THE INVENTION

The present invention concerns and has for its object the provision of novel pharmaceutical compositions comprising a substituted pyrazolidine-3,5-dione according to U.S. Pat. No. 2,700,671, and their use in the treatment of cardiac vascular diseases.

More particularly this invention concerns the novel method for the reduction of sudden cardiac death among subjects who have survived at least one recent myocardial infarction, comprising the enteral administration of pharmaceutical compositions at the significantly higher dosage of about 800 mg of sulfinpyrazone, or its congeners according to the above patent, daily in divided unit dosages during most of the significantly shorter period of months 2 to 12 post infarction. Said changes in dosage and treatment duration, as compared with those published in said Hamilton Symposium report, resulted in a far superior "prevention of death from vascular disease."

This invention relates particularly also to the use of 1,2-diphenyl-4-(2-phenylthioethyl)-pyrazolidine-3,5-dione, or its congeners and salts according to said patent, as the active ingredients of pharmaceutical compositions inhibiting thrombocyte aggregation, particularly for the treatment of thrombotic diseases, as well as novel pharmaceutical compositions containing said active ingredients.

DESCRIPTION OF THE PREFERRED EMBODIMENTS

Said substituted pyrazolidine-3,5-diones are preferably compounds of the formula

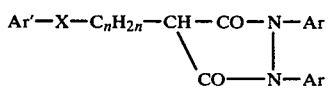

wherein Ar represents phenyl, (lower alkoxy)-phenyl, or (lower alkylthio)-phenyl, Ar' represents phenyl, tolyl, (lower alkoxy)-phenyl or (halogeno)-phenyl, X represents oxy, thio, sulfinyl or sulfonyl and n is an integer from 1 to 4; or pharmaceutically acceptable salts thereof with bases.

In the above-mentioned moieties alkoxy preferably represents methoxy or ethoxy; alkylthio stands especially for methylthio or ethylthio and halogeno is preferably chloro or bromo.

Salts of the depicted pyrazolidine-3,5-diones, or their tautomeric 3- or 5-hydroxy-analogs respectively, are preferably pharmaceutically acceptable metal or ammonium salts, particularly alkali or alkaline earth metal salts, e.g. the sodium, potassium, magnesium or calcium salt, but also, for example, the zinc or copper salt. Said ammonium salts are either derived from ammonia or organic amines, such as mono-, di- or tri-lower (alkyl or hydroxyalkyl)-amines, lower alkylenediamines or lower hydroxyalkyl- or aralkyl-alkyl-ammonium bases, e.g. methylamine, diethylamine, triethylamine, triethanolamine, ethylene-diamine, tri-hydroxymethyl-ethylammonium hydroxide or benzyl-trimethyl-ammonium hydroxide.

The term "lower", as used above and hereinater, defines such organic groups or compounds containing up to 7, preferably up to 4, and especially 1 or 2 carbon atoms.

Sulfinpyrazone is the racemic compound of the above formula, wherein each of Ar and Ar' represents phenyl, X is sulfinyl (SO) and $C_nH_{2n}$ is ethylene, or $(CH_2)_2$ respectively, i.e., the fourth compound listed in column 5 of said U.S. Pat. No. 2,700,671.

The 1,2-diphenyl-4-(2-phenylthioethyl)-pyrazolidine-3,5-dione has the above formula with $Ar=Ar'=$ phenyl, X is thio (S) and $C_nH_{2n}=(CH_2)_2$, i.e., it is the compound of example 3 of said patent. It is also described in Helv. Clin. Acta 44, 232 (1961). It has been shown in experimental arrangements verifying antithrombotic effects, especially in cyclooxygenase-dependent tests, that said 1,2-diphenyl-4-(2-phenylthioethyl)-pyrazolidine-3,5-dione, and salts thereof, have an about ten times greater effect than such of sulfinpyrazone. This outstanding antithrombotic activity can also be demonstrated by means of the Arthus-reaction according to Brit. J. Pharmacol. 57, 441 P (1976), at the dosage range between about 5 and 50 mg/kg/day orally. Also in vitro said compound shows in the concentration range between about 75 and 750 mg/L activity in the prostaglandin-synthetase inhibition from arachidonic acid.

Accordingly, said compounds and compositions are excellently suitable for the treatment of thrombotic diseases, for example in the case of myocardial infarction for the prevention of sudden cardiac death, and/or as antithrombotic agents for other related ailments.

In the outset of this invention it was assumed that among said subjects the first-year mortality rate would be approximately 10 percent and that sulfinpyrazone would reduce this rate to 5 percent. It was calculated that, allowing for dropouts and exclusions, approximately 1200 patients would be needed to ensure an adequate number of eligible patients required for a two-tailed test on proportions. These calculations were based on selected alpha (Type 1 error probability) and 1-beta (chance of detecting the hypothesis of interest) values of 0.05 and 0.90, respectively. Treatment-efficacy comparisons were based on Cox's regression models and life-table methods. Survivorships of all patients, as of July 31, 1977, regardless of their extent of participation, was accounted for through individual follow-up observation.

Patient assignment to trial therapy was randomized at the co-ordinating center, where numerical randomization schedules were developed separately for each investigational center. Drug assignments were preset in blocks of 10 with an equal number of patients receiving placebo and sulfinpyrazone in each block. The order of drug assignment was randomly computer-generated with each block 10.

In accordance with pre-established policies, upon enrollment of approximately 1200 patients the special statistical consultant assessed all collected data and found significant differences in cardiac mortality between therapy groups. On the basis of this finding, he recommended review of the data when approximately 1500 eligible patients had entered the trial and significant differences in cardiac mortality were still maintained.

Said subjects were male and female patients, 45 to 70 years of age, with at least one myocardial infarction, the most recent of which occurred 25 to 35 days before enrollment in the study. The qualifying event was objectively documented with positive electrocardiographic findings, typical chest-pain symptoms and serum enzyme concentrations compatible with an acute myocardial infarction. Serum enzyme concentrations must have reached their peak within 72 hours of the onset of symptoms, with at least two values of serum glutamic oxalacetic transaminase, lactic dehydrogenase or creatine phosphokinase exceeding twice the upper limits of normal. Only patients rated acutely as Killip Class I or II were elegible for inclusion. Previous cardiac operation, cardiomegaly (cardiothoracic ratio greater than 55 percent) demonstrated untreated coagulants or agents known to affect platelet function, including dipyridamole, clofibrate or aspirin, excluded patients from participation in the study. Concomitant use of all other pharmacologic agents commonly used in the management of patients after myocardial infarction were permitted. Patients who underwent cardiac operations (including aortocoronary bypass) after entry into the trial were permitted to continue.

Observation periods range from a minimum of one to a maximum of two years at the conclusion of the trial. Base-line clinical and laboratory observations are made 25 to 35 days after the qualifying infarction. The laboratory studies included hemoglobin, hematocrit, leukocyte count and differential, serum uric acid, alkaline phosphatase, creatinine, potassium, sodium chloride, glucose, cholesterol, gultamic oxalacetic transaminase, total bilirubin, blood urea nitrogen, urinalysis, platelet count and prothrombin and partial thromboplastin times. Interim history, physical and laboratory observations are made at one, two, six 12, 18 and 24 months, with electrocardiographic analysis at one, 12, and 24 months. Additional visits at four, eight, 10, 14, 15, 10 and 22 months monitor toxicity and compliance. The patient or physician may initiate withdrawal from the trial at any time for medical or nonmedical reasons.

Compliance with trial therapy is assessed by tablet counts and measured depression of serum acid levels. Serum uric acid determinations, carried out by the central laboratory facility, are not made available to the investigational centers. Patients with an unexplained overall compliance by tablet count of less than 80 percent at three consecutive visits are dropped from the trial.

Because the principal end point is cardiac mortality it was necessary to establish criteria to assure appropriate categorization of deaths. These criteria were set before the onset of the trial and are applied consistently. Deaths are reviewed, and diagnoses set and categorized as "analyzable" or "nonalayzable" by the appropriate trial committees without knowledge of medication received. Analyses of mortality data are carried out on "analyzable" events. These events are those that occurred more than seven days after initiation of the trial therapy or less than seven days after withdrawal of therapy. This "seven-day rule" was based on findings indicating the onset of clinically beneficial therapeutic effect of sulfinpyrazone after seven days' exposure and loss of benefit at seven days after cessation of therapy. However, events occurring seven days after withdrawal from therapy are included when the event can be established as having been associated with a nonfatal event occurring within the limits described above.

All fatal events not eligible for efficacy analyses ("nonalayzable") were tabulated separately. These events included surgical deaths in which no association could be established with a nonfatal event within the limits described above.

According to the method of this invention, said subjects received 800 mg of sulfinpyrazone orally in pharmaceutical unit dosages of 200 mg tablets four times a day. However, 400 mg or 200 mg capsule unit dosages may also be administered two or four times a day respectively. This medication reduced the serum uric acid levels consistently to about 70% of the baseline value in 89% of the patients. Eight percent were found to have fluctuating serum uric acid values that could be correlated with a medical explanation or interruption of therapy. Only 3% demonstrated an unexplained variation in serum uric acid level.

Drug compliance, as measured by tablet counts, was determined for the entire sample. Eighty-seven percent of the total sample demonstrated an overall therapy compliance rate of about 80%. An overall compliance rate of less than 80% in 5% of the sample was explained by a documented medical or other valid reasons for interruption of therapy. Only 2% of the sample demonstrated less than 80% compliance that was unexplained. Six percent of the patients had insufficient exposure to therapy (baseline visit only) for compliance to be evaluated.

According to the results obtained for the method of this invention the annual total death rate, corrected for exposure time, was 9.5% in the placebo group and 5.1% in the sulfinpyrazone group, representing a 46.4% reduction in overall death rate. The annual cardiac-death rate corrected for exposure time—9.5% in the placebo group and 4.9% in the sulfinpyrazone group—represents a 48.5% reduction in overall cardiac mortality in the sulfinpyrasone group ($P=0.011$ when unadjusted and 0.018 when adjusted for baseline characteristics).

Sixty-one percent of all deaths were sudden cardiac deaths. The annual sudden-cardiac-death rate corrected for exposure time was 6.3% in the placebo group and 2.7% in the sulfinpyrazone group. This finding represents an observed overall sudden-cardiac-death reduction of 57.2% attributable to sulfinpyrazone ($P=0.012$ unadjusted and 0.015 adjusted). Thirty percent of all deaths were due to myocardial infarction, 7.3% were of an "other cardiac" nature.

Pharmaceutical compositions of said substituted pyrazolidine-3,5-diones comprise an effective amount thereof in conjunction or admixture with conventional excipients suitable for enteral or parenteral, such as oral, rectal or intravenous administration. Preferred are tablets, dragees and gelatin capsules comprising the active ingredient together with (a) diluents, e.g., lactose, dextrose, sucrose, mannitol, sorbitol, cellulose, calcium phosphates and/or glycine, (b) lubricants, e.g., silica, talcum, stearic acid, its magnesium or calcium salt and/or polyethyleneglycol, for tablets also, (c) binders, e.g., magnesium aluminum silicate, starch paste, gelatin, tragacanth, methylcellulose, sodium carboxymethylcellulose and/or polyvinylpyrrolidone, if desired, (d) disintegrants, e.g., starches, agar, alginic acid or its sodium salt, enzymes of the binders or effervescent mixtures and/or, (e) absorbents, colorants, flavors and sweeteners. Dragee cores are provided with suitable coatings, which may be resistant to gastric juices. Coating solutions are, for example, concentrated aqueous sugar solutions, which may contain gum arabic, polyvinylpyrrolidone, polyethylene glycol, talcum and/or titanium dioxide. Said resistant coatings are obtained with lacquer solutions in organic solvents, such as shellac, acetylcellulose phthalate or hydroxypropylmethylcellulose phthalate in ethanol and the like. Dyestuffs or pigments may be added for identification of brand name and dose. Capsules are either made from hard gelatine, or they are soft, closed capsules made from gelatine and a softener, e.g., glycerin or sorbitol. The hard capsules contain either uncompressed powder mixtures, e.g., those mentioned under (a) and (b), or granulates similar to those used for tablets. In the soft capsules said active ingredients are preferably dissolved or suspended in suitable liquids, such as fatty oils, paraffins, or polyethylene glycols. Suppositories are advantageously solid, fatty emulsions or suspensions, containing the active ingredient, for example, in natural or synthetic triglycerides, paraffins, waxes and/or polyethylene glycos.

Compositions for parenteral administration are preferably aqueous solutions or suspensions of said active substances, but also oily solutions or suspensions thereof, e.g., natural or synthetic fatty oils, such as sesame oil or ethyl oleate, in suitable ampules.

Said compositions may be sterilized and/or contain adjuvants, such as preserving, stabilizing, wetting or emulsifying agents, solution promoters, salts for regulating the osmotic pressure and/or buffers. They may also contain other therapeutically valuable substances, and are prepared according to conventional mixing, granulating or coating methods respectively. They may contain from 10 to 95%, preferably from about 20 to 70% of the active ingredient. Individual unit dosages thereof contain preferably between about 50 and 400 mg, advantageously about 100 or 200 mg of said active ingredients, and the daily dose may reach 1,000 mg, preferably 800 mg per subject of approximately 75 kg body weight.

The following examples are intended to illustrate the invention and are not to be construed as being limitations thereon. All parts wherever given are parts by weight. The "Active ingredient" mentioned therein is preferably either sulfinpyrazone, or 1,2-diphenyl-4-(2-phenylthioethyl)-pyrazolidine-3,5-dione, but may also be a congener thereof encompassed by the above structural formula, or a salt thereof.

EXAMPLE 1

Preparation of 1,000 sugar-coated tablets each containing 200 mg of the active ingredient.

| Formula of the core: | |
| --- | --- |
| Active ingredient | 200.0 g |
| Corn starch | 58.0 g |
| Lactose | 15.3 g |
| Stearic acid | 6.0 g |
| Gelatin | 6.0 g |
| Glycerin | 1.7 g |
| Talc | 12.0 g |
| Magnesium stearate | 1.0 g |
| Ethanol anhydrous | q.s. |
| Water | q.s. |

Procedure:

The active ingredient, starch and lactose are blended in a suitable mixer. The stearic acid is dissolved in hot ethanol, and the gelatin and glycerin in hot water. Both solutions are added to the blended powders to granulate them. The resulting granulation is dried, passed through a screen with 1.2 mm openings, blended with the talc and magnesium sterate and compressed into 300 mg tablet cores.

| Formula of the coating: | |
| --- | --- |
| Shellac solution solids | 2.40 g |
| Talc | 22.00 g |
| Titanium dioxide | 2.50 g |
| Castor oil | 0.30 g |
| Sucrose | 119.06 g |
| Polyvinylpyrrolidone | 1.56 g |
| Microcrystalline cellulose | 1.04 g |
| Polyethyleneglycol 6.000 | 1.04 g |
| Sucrose with 3% corn starch | 1.03 g |
| Carnauba Wax | 0.07 g |

-continued

| Formula of the coating: | |
|---|---|
| Ethanol anhydrous | q.s. |
| Water | q.s. |

Procedure:

A sealing solution is made up of the shellac solution, ethanol and caster oil in a suitable coating pan. The tablet cores are dusted with the talc and titanium dioxide, while drying, if necessary. Sufficient coating of the sucrose-water syrup is applied, the cores are dusted with the sucrose starch mix, and dried if necessary. Sufficient grossing syrup, made up of polyethyleneglycol, ethanol, polyvinylpyrrolidone, coating syrup, cellulose, titanium dioxide and talc is applied and the cores are dried, if necessary. Thereupon, sufficient applications of coating syrup and titanium dioxide-colored syrup are made while drying, if necessary, between the applications. The resulting coated 450 mg tablets are finally polished with carnauba wax and brand-printed, if desired.

EXAMPLE 2

Preparation of 1,000 capsules each containing 200 mg of the active ingredient.

| Formula: | |
|---|---|
| Active ingredient | 200.0 g |
| Corn starch | 29.0 g |
| Gelatin | 6.5 g |
| Lactose | 90.0 g |
| Magnesium stearate | 3.5 g |
| Stearic acid | 3.0 g |
| Talc | 3.5 g |
| Isopropanol | q.s. |
| Water | q.s. |

Procedure:

The active ingredient, 20 g of the starch and the lactose are blended in a suitable mixer. The stearic acid is dissolved in hot isopropanol and the gelatin in hot water. Both solutions are added to the powders and the resulting granulation wetted, if necessary, with water. It is passed through a comminuting machine, dried and the granules blended with the remaining 9 g of starch, the talc and the magnesium stearate. The completed blend is encapsulated in No. 1 hard gelatin capsules and brand-printed with edible ink, if desired.

EXAMPLE 3

Preparation of 1,000 capsules each containing 100 mg of active ingredient.

| Formula: | |
|---|---|
| Active ingredient | 100.0 g |
| Corn starch | 10.0 g |
| Gelatin | 2.0 g |
| Lactose | 173.0 g |
| Talc | 15.0 g |
| Water | q.s. |

Procedure:

The active ingredient is mixed with the lactose, the mixture evenly moistened with an aqueous solution of the gelatin, granulated through a sieve No. 3, the granulate is dried, mixed with the starch and then with the talc and filled into 1,000 hard gelatine capsules No. 1.

EXAMPLE 4

Preparation of 1 ml ampules for injection containing 100 mg of active ingredient.

| Formula: | |
|---|---|
| Active ingredient | 10.0 g |
| Benzyl alcohol | 1.0 g |
| Sodium sulfite | 0.1 g |
| Disodium edetate | 0.2 g |
| Vitamin C | 0.3 g |
| Water | q.s. |

Procedure:

The above ingredients are dissolved in about 80 ml of pyrogen-free water, the solution adjusted to pH=8.6 with aqueous sodium hydroxide and the whole made up with water to 100 ml. The solution is filtered, filled into 1 ml ampules, which are conventionally sealed and sterilized.

What is claimed is:

1. A method for reducing the mortality rate among subjects who have survived at least one recent myocardial infarction, comprising the enteral administration of pharmaceutical compositions containing about 800 mg of a compound of the formula

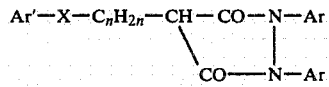

wherein Ar represents phenyl, (lower alkyl)-phenyl or (lower alkoxy)-phenyl, Ar' stands for phenyl, tolyl, (lower alkoxy)-phenyl or (halogeno)-phenyl, X represents oxy, thio, sulfinyl or sulfonyl and n is an integer from 1 to 4, or a pharmaceutically acceptable salt thereof; daily in divided unit dosages during the period of months 2 to 12 post infarction.

2. A method according to claim 1, wherein said compositions are orally administered.

3. A method according to claim 1, wherein said compositions consist of tablets containing about 100 to 400 mg of sulfinpyrazone each.

4. A method according to claim 1, wherein said compositions consist of capsules containing about 100 to 400 mg of sulfinpyrazone each.

5. A method according to claim 3, wherein 200 mg sulfinpyrazone tablets are orally administered four times a day.

6. A method according to claim 4, wherein 200 mg sulfinpyrazone capsules are orally administered four times a day.

7. A method according to claim 1, wherein said composition comprising 1,2-diphenyl-4-(2-phenylthioethyl)-pyrazolidine-3,5-dione, or a pharmaceutically acceptable salt thereof, in individual doses suitable for enteral or parenteral administration of a daily dosage of up to 800 mg of said active substance.

8. A method according to claim 7 wherein said composition is suitable for oral administration.

9. A method according to claim 8 wherein said composition is suitable for administration as tablets each containing 50 to 200 mg of free active substance.

10. A method according to claim 8 wherein said composition is suitable for administration as capsules each containing 50 to 200 mg of free active substance.

11. The use of 1,2-diphenyl-4-(2-phenylthioethyl)-pyrazolidine-3,5-dione, or a pharmaceutically acceptable salt thereof for the treatment of survivors of myocardial infarction, according to the method of claim 1.

12. The use of the 1,2-diphenyl-4-(2-phenylthioethyl)-pyrazolidine-3,5-dione, or a pharmaceutically acceptable salt thereof for the treatment of survivors of myocardial infarction caused by thrombotic diseases, according to the method of claim 1.

13. The use of the 1,2-diphenyl-4-(2-phenylthioethyl)-pyrazolidine-3,5-dione, or of a pharmaceutically acceptable salt thereof for the treatment of survivors of myocardial infarction caused or accompanied by an abnormal function of the blood platelets according to the method of claim 1.

14. The use of 1,2-diphenyl-4-(2-phenylthioethyl)-pyrazolidine-3,5-dione, or a pharmaceutically acceptable salt thereof according to the method of claim 1, wherein administration is effected enterally or parenterally.

15. The use of 1,2-diphenyl-4-(2-phenylthioethyl)-pyrazolidine-3,5-dione, or of a pharmaceutically acceptable salt thereof, according to the method of claim 1, wherein administration is effected orally.

16. The use of 1,2-diphenyl-4-(2-phenylthioethyl)-pyrazolidine-3,5-dione, or of a pharmaceutically acceptable salt thereof, according to the method of claim 1, wherein administration is effected in individual doses of 50 to 200 mg in the form of tablets, capsules or dragees.

* * * * *

UNITED STATES PATENT AND TRADEMARK OFFICE
CERTIFICATE OF CORRECTION

PATENT NO. : 4,255,438
DATED : March 10, 1981
INVENTOR(S) : Sydney H. Kane and Erwin Margulies It is certified that error appears in the above-identified patent and that said Letters Patent are hereby corrected as shown below:

Claim 3, column 8, line 44 reads:

"mg of sulfinpyrazone each".

Should read:

"mg of sulfinpyrazone".

Claim 4, column 8, line 48 reads:

"mg of sulfinpyrazone each".

Should read:

"mg of sulfinpyrazone".

Signed and Sealed this

Thirtieth Day of June 1981

[SEAL]

Attest:

Attesting Officer

RENE D. TEGTMEYER

Acting Commissioner of Patents and Trademarks